United States Patent
Krupenkin et al.

(10) Patent No.: US 10,264,846 B2
(45) Date of Patent: Apr. 23, 2019

(54) METHOD AND APPARATUS FOR PROVIDING INTERNAL HEATING OF FOOTWEAR

(71) Applicants: Thomas Nikita Krupenkin, Madison, WI (US); Joseph Ashley Taylor, Madison, WI (US)

(72) Inventors: Thomas Nikita Krupenkin, Madison, WI (US); Joseph Ashley Taylor, Madison, WI (US)

(*) Notice: Subject to any disclaimer, the term of this patent is extended or adjusted under 35 U.S.C. 154(b) by 116 days.

(21) Appl. No.: 15/407,305

(22) Filed: Jan. 17, 2017

(65) Prior Publication Data
US 2017/0119089 A1    May 4, 2017

Related U.S. Application Data

(62) Division of application No. 14/146,034, filed on Jan. 2, 2014, now Pat. No. 9,572,393.

(60) Provisional application No. 61/748,527, filed on Jan. 3, 2013.

(51) Int. Cl.
| | | |
|---|---|---|
| *A43B 7/02* | (2006.01) | |
| *A43B 5/04* | (2006.01) | |
| *H02N 11/00* | (2006.01) | |
| *H02N 1/08* | (2006.01) | |
| *A43B 13/18* | (2006.01) | |
| *F15B 7/00* | (2006.01) | |
| *A61F 7/00* | (2006.01) | |

(52) U.S. Cl.
CPC ............ *A43B 7/02* (2013.01); *A43B 5/0407* (2013.01); *A43B 13/189* (2013.01); *F15B 7/001* (2013.01); *H02N 1/08* (2013.01); *H02N 11/002* (2013.01); *A61F 2007/0045* (2013.01)

(58) Field of Classification Search
CPC ......... A43B 7/02; A43B 7/001; A43B 5/0407; A43B 13/189
See application file for complete search history.

(56) References Cited

U.S. PATENT DOCUMENTS

| | | |
|---|---|---|
| 2,648,784 A | 8/1953 | Chilowsky |
| 3,952,577 A | 4/1976 | Hayes et al. |
| 4,446,634 A | 5/1984 | Johnson |
| 4,799,319 A | 1/1989 | Zellweger |

(Continued)

FOREIGN PATENT DOCUMENTS

| | | |
|---|---|---|
| JP | 2007325836 | 12/2007 |
| JP | 2008208766 | 9/2008 |

(Continued)

*Primary Examiner* — Jila M Mohandesi
(74) *Attorney, Agent, or Firm* — Wendy W. Koba

(57) ABSTRACT

A method and apparatus for generating thermal energy (heat) from human locomotion is proposed and used to provide heating of the user's footwear. The apparatus takes the form of a pair of flexible, liquid-filled chambers connected by an energy-generating tube. One chamber is located in the heel region of a footwear insole, with the other in the toe region, such that as a person walks, the liquid moves back and forth within the tube. This movement is used to also move an energy-producing element (either an electromagnetic arrangement or viscous liquid) back and forth within the tube and convert the captured human locomotion energy into thermal energy, thus warming the footwear.

4 Claims, 7 Drawing Sheets

(56) References Cited

U.S. PATENT DOCUMENTS

| | | | |
|---|---|---|---|
| 5,228,217 A * | 7/1993 | Dabuzhsky | A43B 17/026 |
| | | | 36/28 |
| 5,499,460 A | 3/1996 | Bryant | |
| 5,806,208 A | 9/1998 | French | |
| 5,953,834 A | 9/1999 | Clodic | |
| 6,092,310 A * | 7/2000 | Schoesler | A43B 17/035 |
| | | | 36/153 |
| 6,201,314 B1 | 3/2001 | Landry | |
| 6,239,501 B1 | 5/2001 | Komarechka | |
| 6,745,499 B2 | 6/2004 | Christensen | |
| 6,865,825 B2 | 3/2005 | Bailey, Sr. et al. | |
| 7,080,467 B2 * | 7/2006 | Marvin | A43B 13/189 |
| | | | 36/28 |
| 7,186,957 B2 | 3/2007 | Martin | |
| 7,219,449 B1 | 5/2007 | Hoffberg | |
| 7,353,625 B2 * | 4/2008 | Ellis | A43B 7/144 |
| | | | 36/28 |
| 8,176,880 B2 | 5/2012 | Hurwitz | |
| 8,873,914 B2 | 10/2014 | Ellis | |
| 9,109,583 B2 | 8/2015 | Krupenkin | |
| 9,259,047 B2 | 2/2016 | Krupenkin | |
| 2002/0164474 A1 | 11/2002 | Buckley | |
| 2006/0060185 A1 | 3/2006 | Dehn | |
| 2008/0197126 A1 | 8/2008 | Bourke et al. | |
| 2011/0192834 A1 | 8/2011 | Muller et al. | |
| 2011/0247235 A1 | 10/2011 | de Roode | |
| 2012/0124717 A1 | 5/2012 | Austin | |
| 2012/0260522 A1 | 10/2012 | Shi et al. | |

FOREIGN PATENT DOCUMENTS

| | | |
|---|---|---|
| KR | 20-0291766 | 10/2002 |
| KR | 10-20070049614 | 5/2007 |

\* cited by examiner

METHOD AND APPARATUS FOR PROVIDING INTERNAL HEATING OF FOOTWEAR

CROSS-REFERENCE TO RELATED APPLICATIONS

This application is a divisional of U.S. patent application Ser. No. 14/146,034, filed Jan. 2, 2014, which claims the benefit of U.S. Provisional Application Ser. No. 61/748,527, filed Jan. 3, 2013 and herein incorporated by reference.

TECHNICAL FIELD

The present invention relates to a method and apparatus for heating footwear (such as insoles) and, more particularly, to a heating method and apparatus based on human locomotion to eliminate the need to recharge and/or replace traditional footwear heating products.

BACKGROUND OF THE INVENTION

High-power harvesting of mechanical energy from human locomotion is a well-known concept, but has not been widely commercialized to date due to the lack of viable energy harvesting technologies. One of the potentially important applications of high-power harvesting of mechanical energy from human locomotion is the heating of footwear—particularly outdoor footwear used in cold climates.

There are a number of popular products that are currently available to provide heat for outdoor footwear, including electrical heaters powered by batteries and specially-designed footwear inserts that chemically generate heat (i.e., an exothermic reaction upon activation of the insert). However, both of these types of devices have several drawbacks. These include the need to replace or recharge batteries for the electrical heaters, as well as the disposal and replacement of the exothermic elements once the chemical reaction has been exhausted.

SUMMARY OF THE INVENTION

The limitations of the prior art as described above are addressed by the present invention, which relates to a method and apparatus for heating footwear (such as insoles) and, more particularly, to a heating method and apparatus based on human locomotion to eliminate the need to recharge and/or replace traditional footwear heating products. The energy-producing arrangement is sized to fit within an inner sole of footwear, with human locomotion used to move an energy-generating mechanism within an energy-generating tube.

In accordance with one embodiment of the present invention, an energy-producing arrangement takes the form of a tube having spaced-apart segments of conductive material, with a chain of spaced-apart magnetic segments disposed within the tube. The energy-producing chain is configured to slide along within the tube in response to the impression of a mechanical force on the tube (e.g., via human locomotion). Each time a magnetic segment aligns with a segment of conductive material, an eddy current is generated within the conductive material, creating resistive heat. The total amount of heat that is generated is thus dependent upon the number of individual segments used to form the energy-generating tube and chain.

Another embodiment of the present invention takes the form of a viscous fluid that flows back and forth within a tube (between a heel reservoir and toe reservoir during human locomotion, for example), dissipating energy and creating heat. The viscosity of the fluid, in combination with the dimensions of the tube, determines the amount of heat that may be generated.

One particular embodiment of the present invention takes the form of an apparatus for converting mechanical energy into thermal energy, including a first flexible chamber containing a quantity of liquid, a second flexible chamber containing a quantity of liquid, an energy-generating tube coupled to the first and second flexible chambers in a manner such that liquid flows back and forth within the tube as a function of mechanical pressure applied in alternating fashion to the first and second flexible chambers and an energy-producing element disposed within the energy-generating tube, wherein the liquid flow induced by mechanical pressure creates movement of the energy-producing element within the energy-generating tube, generating thermal energy as a function of the movement of the energy-producing element.

Another embodiment of the present invention takes the form of a method of converting mechanical energy into thermal energy for heating footwear including the steps of: providing an energy harvesting apparatus including a first flexible chamber containing a quantity of liquid, a second flexible chamber containing a quantity of liquid, an energy-generating tube coupled to the first and second flexible chambers such that the liquid flows within the tube between the first and second flexible chambers, and an energy-producing element disposed within the energy-generating tube in a manner such that the energy-producing element is free to move back and forth within the energy-generating tube; applying a mechanical pressure to the first flexible chamber, forcing a portion of the contained liquid into the energy-generating tube, moving the energy-producing element toward the second flexible chamber; removing the mechanical pressure applied to the first flexible chamber; applying a mechanical pressure to the second flexible chamber, forcing a portion of the contained liquid into the energy-generating tube, moving the energy-producing element toward the first flexible chamber, and continuing to alternate the application of pressure between the first and second flexible chambers so as to provide movement of the energy-producing element back and forth within the energy-generating tube, converting the applied mechanical pressure into thermal energy.

Other and further embodiments of the present invention will become apparent during the course of the following discussion and by reference to the accompanying drawings.

BRIEF DESCRIPTION OF THE DRAWINGS

Referring to the drawings, where like numerals represent like parts in several views.

DETAILED DESCRIPTION

As will be described in detail below, various embodiments of the present invention take the form of a pair of spaced-apart liquid-filled flexible chambers and energy-generating tubing that interconnects the pair of chambers. This combination is inserted within a shoe/boot (or incorporated within a midsole positioned within the footwear). Human locomotion, in the form of walking or running, causes the back and forth movement of energy-generating material within the tube, converting this motion into thermal energy that is sufficient to warm the feet of the user.

Figure 1:
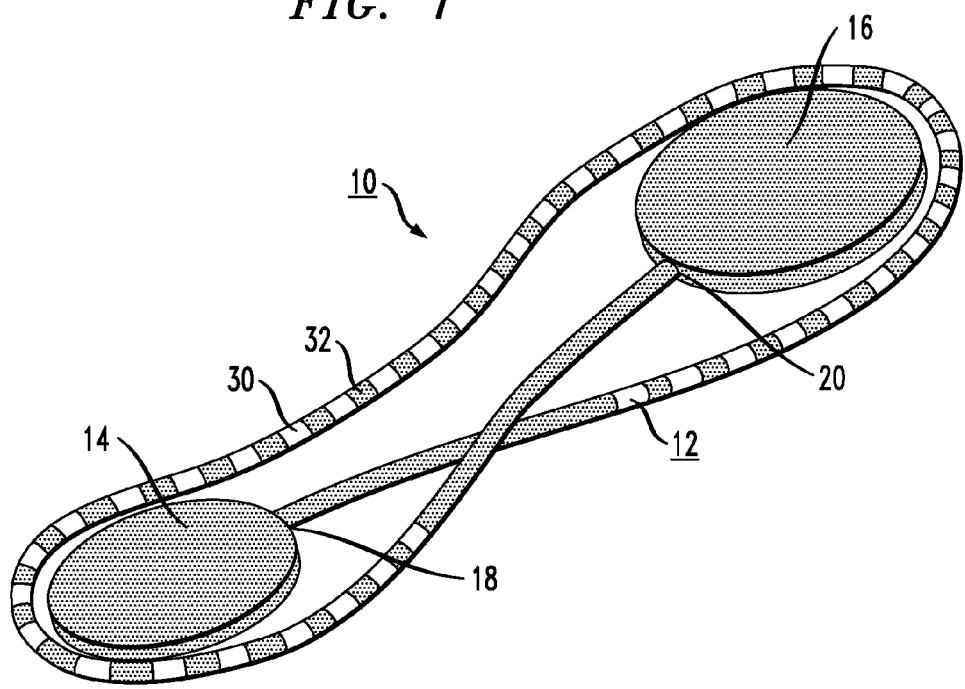
FIG. 1 is an isometric view of an exemplary human locomotion-based footwear heater apparatus formed in accordance with an embodiment of the present invention.

FIG. 1 presents a schematic view of one exemplary embodiment of the present invention for capturing mechanical energy from human locomotion and converting it into thermal energy, particularly useful in generating heat for footwear. In this particular arrangement, an apparatus 10 is configured to produce reciprocating (or circular) motion of an energy-generating chain (not shown) within an energy-generating tube 12.

As shown, apparatus 10 also comprises a pair of flexible chambers 14 and 16, each containing a volume of an inert dielectric liquid. In this particular configuration where apparatus 10 is to be used as an insole for footwear, flexible chamber 14 is located at the heel area and flexible chamber 16 is located at the front, toe area of an insole. Chambers 14 and 16 are shown as connected to energy-generating tube 12 at ports 18 and 20, respectively. During a heel strike, chamber 14 will be compressed, causing a portion of the inert fluid in chamber 14 to be displaced and enter tube 12. As will be discussed below, this flow of fluid causes sliding motion of an energy-generating chain (not shown) from heel chamber 14 towards toe chamber 16. During toe-off, the pressure on flexible toe chamber 16 forces the flow of the fluid in the opposite direction, reversing the direction of movement of the energy-generating chain within energy-generating tube 12.

Therefore, as long as an individual contains to walk, the pressure on flexible heel chamber 14 and flexible toe chamber 16 will continue to alternate, maintaining the back-and-forth motion of the energy-generating chain within energy-generating tube 12.

With this understanding of the basic process of energy harvesting by capturing human locomotion and converting it into mechanical energy (in the form of movement of the chain within the tube), the details of generating thermal energy (heat) in accordance with the present invention may be best understood. A more detailed analysis of harvesting human locomotion for energy generation can be found in the inventors' prior work as embodied in, for example, an article entitled *"Reverse electrowetting as a new approach to high-power energy harvesting"*, appearing in Nature Communications, Vol. 2, No. 448, published Aug. 23, 2011.

Figure 2:
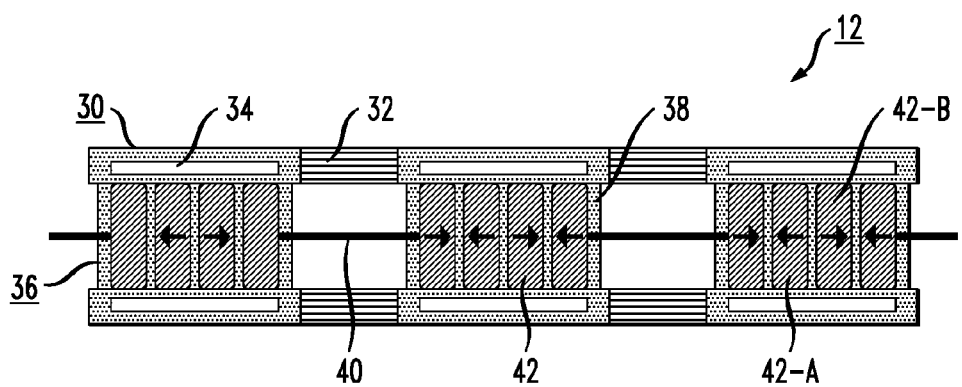
FIG. 2 is a schematic cross-sectional view of a segmented configuration of an energy-generating tube and energy-generating chain that may be used to produce heat as a result of human locomotion in accordance with the present invention.

As mentioned above, thermal energy is created in accordance with the present invention by the back-and-forth movement of an energy-generating chain within an energy-generating tube. FIG. 2 is a cross-sectional diagram of an exemplary portion of energy-generating tube 12 (as shown in FIG. 1), showing a portion of one such exemplary energy-generating chain.

Figure 3:
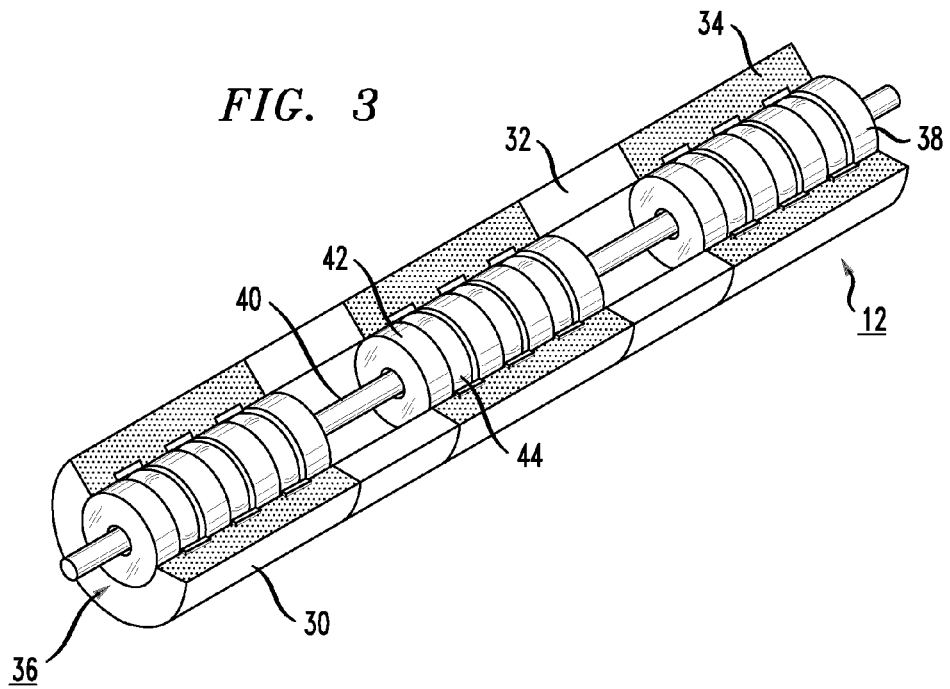
FIG. 3 is another schematic cross-sectional view of the same configuration as FIG. 2, in this case illustrating the relative motion of the energy-generating chain with respect to the energy-generating tube under the influence of human locomotion.
Figure 4:
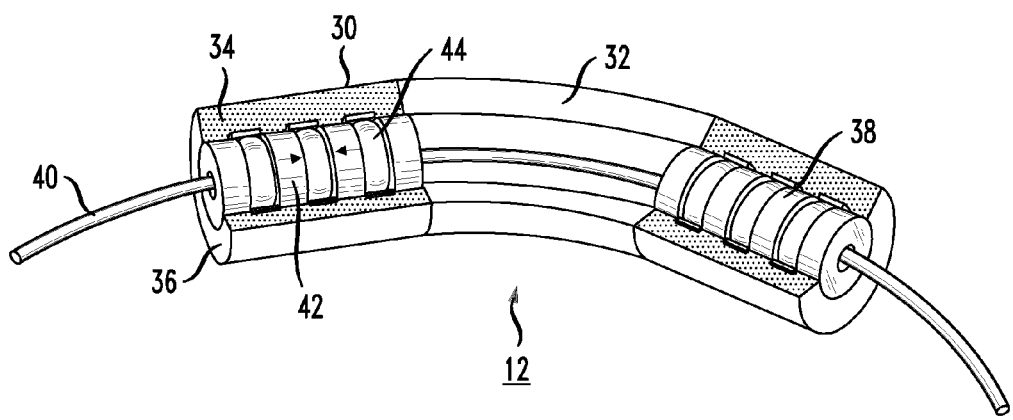
FIG. 4 is an isometric, cut-away view of a section of the apparatus of the present invention.

In this particular embodiment, energy-generating tube 12 is shown as comprising a set of substantially rigid energy-producing modules 30, separated by flexible tube segments 32. Each energy-producing module 30 includes a segment of conductive material 34 that is embedded in the rigid material forming module 30. The utilization of alternating rigid and flexible modules allows for the necessary flexibility of the apparatus, while also providing selected regions where alignment of energy-generating portions of the tube and chain will align. A further analysis of this segmented arrangement can be found in U.S. application Ser. No. 13/967,859, filed Aug. 15, 2013 and herein incorporated by reference. FIG. 3 is an isometric view of this portion of the arrangement of FIG. 2, while FIG. 4 is an isometric view of the same portion, in this case in a "flexed" configuration.

Also shown in FIG. 2 is an energy-generating chain 36 that comprises a set of substantially rigid modules 38 affixed to a flexible string or shaft 40 in such a way that modules 38 will not slide along flexible string 40. In accordance with the present invention, energy-generating chain 36 is disposed within energy-generating tube 12, but remains free to slide back and forth within tube 12. Each rigid module 38 is shown as comprising a set of magnets 42. Neighboring magnets (such as 42-A and 42-B) are magnetized through their thickness in the opposite directions, as schematically shown by arrows in FIG. 2.

As best shown in FIG. 3, neighboring magnets 42 are separated by rigid separators 44 in such a way that magnets 42 do not move with respect to each other. This configuration functions to fix the distance between adjacent magnets 42 and guarantees the exact positioning of the magnets within each rigid module 38. By virtue of including flexible segments 26 along tube 12, and having a flexible string separating adjacent rigid modules 38, the combination is capable of bending, such as when "flexed" during human locomotion, as shown in FIG. 4.

Figure 5:
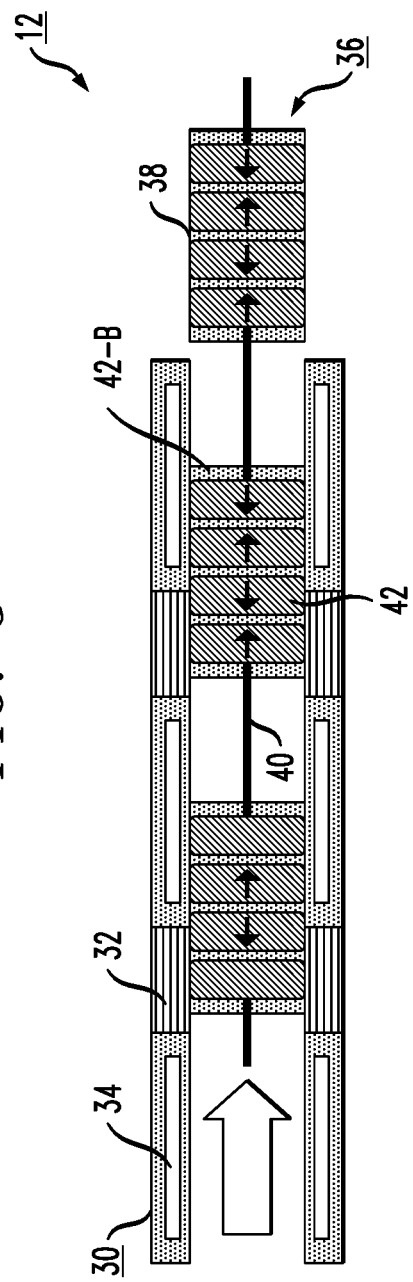
FIG. 5 is another isometric, cut-away view, in this case illustrating the flexibility of the apparatus, by virtue of including flexible sections of tubing between each segment of conductive material forming the energy-generating tube.

As discussed above in association with FIG. 1, as mechanical pressure is alternately applied to heel chamber 14 and toe chamber 16 during human locomotion, the inert liquid within the chambers flows back and forth within tube 12, creating the movement of energy-generating chain 36 within energy-generating tube 12. FIG. 5 is a diagram depicting the same configuration as shown in FIG. 2, in this case where energy-generating chain 36 has slid along within the interior region of energy-generating tube 12. The relative movement of chain 36 with respect to tube 12 is thus evident in this view.

In accordance with this embodiment of the present invention, therefore, as rigid chain modules 38 of energy-generating chain 36 slide along within energy-generating tube 12, magnets 42 within modules 38 will be surrounded by conductive segments 34 of the associated tube rigid modules 30. The overlap of magnets 42 with conductive segments 34 generates electrical eddy currents within each segment 34. The mechanism of the electrical current generation in segment 34 is based on the Faraday's law of electromagnetic induction and is well known to those skilled in the art. The generated eddy currents cause resistive heating of conductive segments 34 within each module 30 forming energy-generating tube 12 and, as a result, cause an increase in the temperature of the whole energy generating tube 12, as well as the fluid in chambers 14 and 16. The increase in temperature thus provides heating of the footwear for the user.

Thus, as long as the user keeps walking, the human locomotion will maintain the generation of thermal energy (heat) from the passing of magnets 42 through conductive segments 34.

Figure 6:
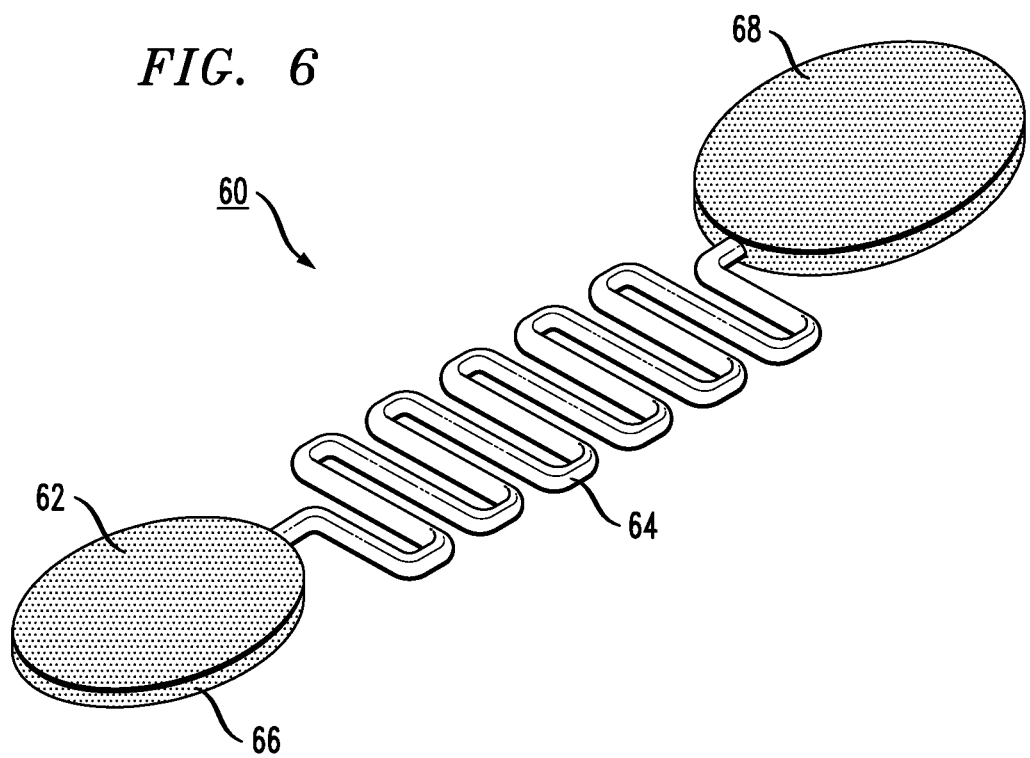
FIG. 6 is an isometric view of an alternative embodiment of the present invention, in this case utilizing a viscous liquid to generate thermal energy as it moves within energy-generating tubing, the energy-generating tubing having a serpentine configuration in this particular embodiment.

In another embodiment of the present invention, viscous energy dissipation is used as a mechanism to convert mechanical energy (from human locomotion) to thermal energy within a footwear insert. As with the arrangement described above, this embodiment comprises a pair of fluid-filled flexible chambers separated by energy-producing tubing. FIG. 6 is a schematic view of one exemplary configuration of this viscous energy dissipation embodiment, in the form of an apparatus 60 for capturing mechanical energy from human locomotion and converting it into thermal energy. Apparatus 60 is adapted to produce an alternating flow of a viscous liquid 62 within an energy-generating tubing 64, where tubing 64 is coupled between a flexible heel chamber 66 and a flexible toe chamber 68. In this embodiment, flexible chambers 66 and 68 are filled with the same viscous liquid 62 as tubing 64.

During human locomotion, the flow of liquid 62 causes viscous energy dissipation within tubing 64 which, in turn, heats the fluid within tubing 64. The thermal energy will then radiate outward from the tubing and flexible chambers, warming the midsole and the user's footwear.

In principle, each time a fluid (such as viscous liquid 62) flows past a solid surface (such as the inner walls of tubing 64), some of the fluid's mechanical energy is converted into heat, due to viscosity. Indeed, it can be shown that viscous energy dissipation (and, as a result, heat) exists in any flow of a fluid, as long as the fluid's spatial velocity distribution has non-zero spatial derivatives (i.e., changes from point to point in space).

Referring to the embodiment as shown in FIG. 6, tubing 64 is formed to exhibit a serpentine shape, allowing tubing 64 to cover a significant portion of the space between the flexible chambers 66 and 68 and thus facilitate uniform heating of the user's footwear.

Figure 7:
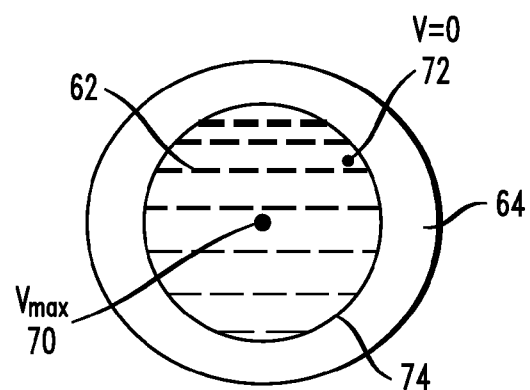
FIG. 7 is a cross-sectional view of a portion of the tubing shown in FIG. 6.
Figure 8:
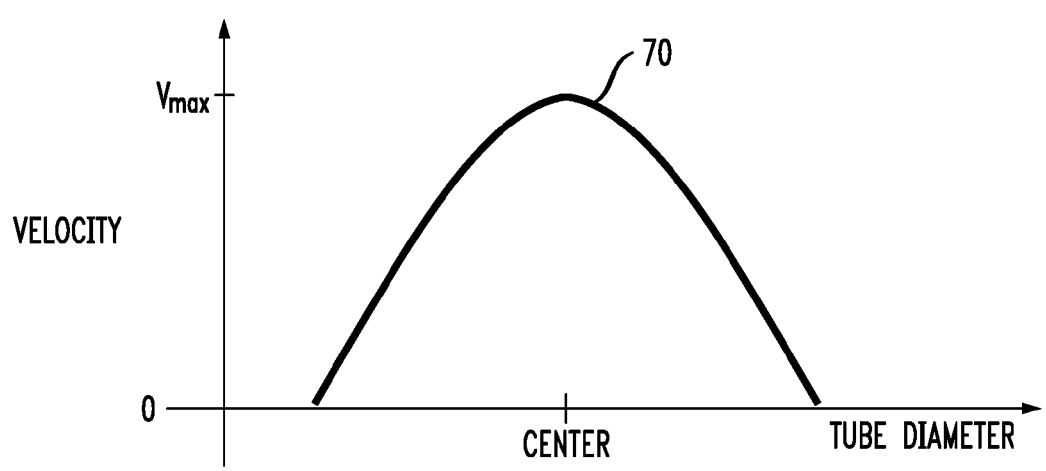
FIG. 8 is a plot of the relative velocity of the viscous liquid across the cross section of the tubing shown in FIG. 7.

Additionally, it is to be understood that the viscosity of liquid 62, as well as the physical parameters of tubing 64, impacts the amount of heat that may be generated by the embodiment of the present invention. For example, when the fluid is flowing through a thin tube, the velocity of the fluid across the tube cross-section will rapidly change, with a maximum velocity achieved in the center region of tubing 64. At the same time, the velocity along the inner walls of tubing 64 is approaching zero. FIG. 7 is a cross-sectional view of an exemplary thin tubing 64, showing a maximum velocity $V_{max}$ of liquid 62 in a central region 70 of tubing 64 while approaching a zero velocity of liquid 62 in a peripheral region 72, near the inner wall surface 74 of tubing 64. FIG. 8 is an exemplary graph depicting a possible rate of change in velocity of fluid 62 across the width of tubing 64 (as shown in FIG. 7), clearly depicting the non-zero spatial derivative of the liquid's velocity. Such rapid spatial change of velocity gives rise to intense energy dissipation and, as a result, heating of the structure forming apparatus 60.

Figure 9:
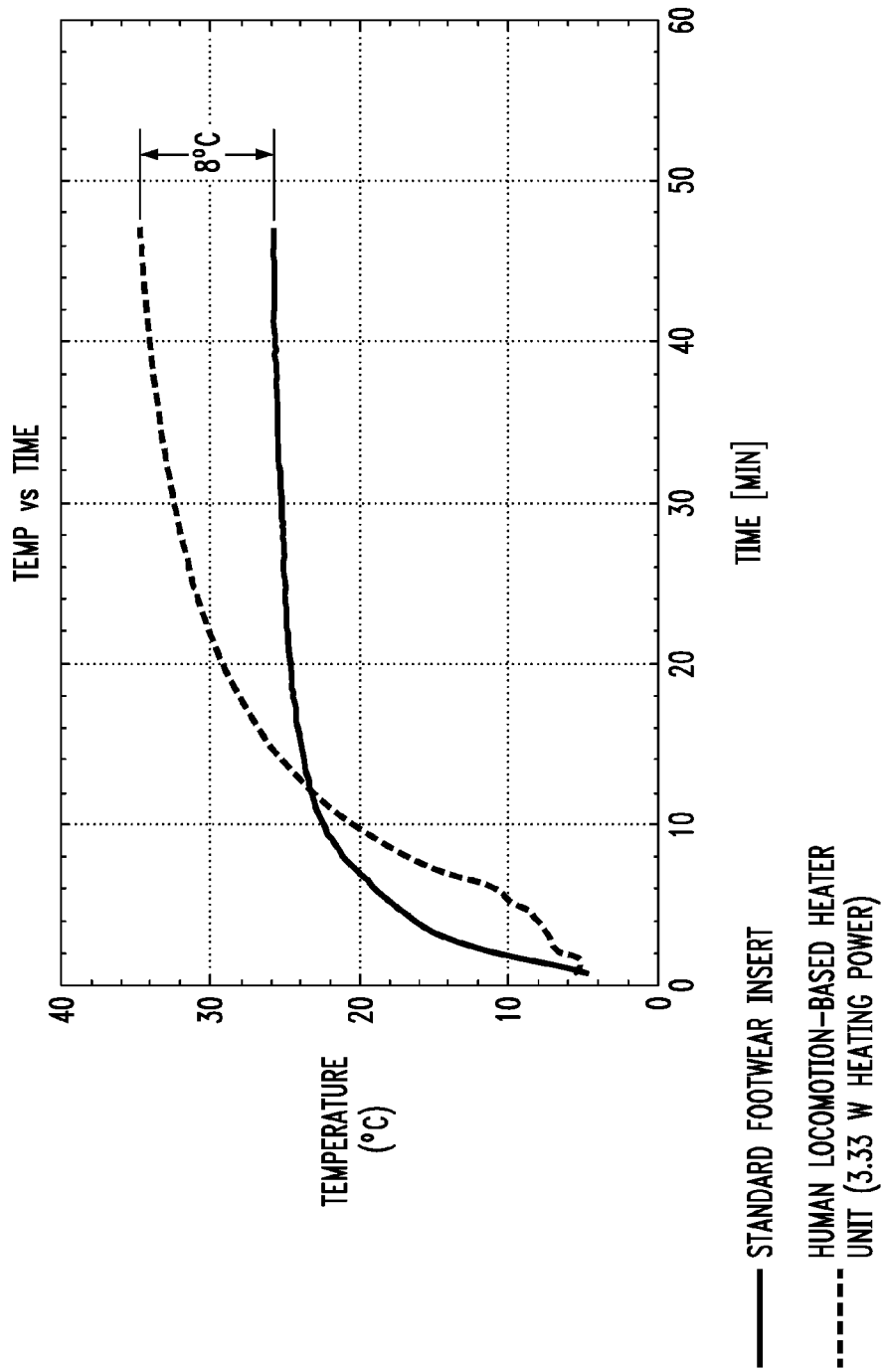
FIG. 9 is a plot of temperature increase as a function of time for both a conventional footwear insert and an energy harvesting-based footwear insert of the present invention, when worn by an individual walking at a controlled pace of about 2 mph.

FIG. 9 illustrates experimental results associated with harvesting mechanical energy to generate heat for footwear in accordance with the present invention. In this case, a configuration similar to that shown in FIG. 6 was used to collect the data, where a relatively small volume (about 25 ml) of viscous fluid having a freezing point less than −30° C. and a melting point greater than +150° C. was inserted in an energy harvesting apparatus consisting of a pair of flexible chambers connected together via energy-generating tubing. This combination of components was then utilized as a footwear insert. For the purpose of analysis, the same footwear was outfitted with a conventional footwear insert (i.e., a regular non-heating footwear insert normally supplied with the boots and used for the comfort of the wearer) was also subjected to the same operating conditions.

That is, for both types of insert, an individual wearing the modified footwear was located in a chamber with an ambient temperature of 0° C., and then asked to walk at an essentially uniform pace of 2 mph. These conditions were found to generate an energy on the order of 3.3 W for the energy harvesting arrangement of the present invention.

After walking for a time period of about forty-five minutes, it can be seen that the inventive energy harvesting warming apparatus was able to achieve a higher temperature (by about 8° C.) than the conventional footwear insert. This result has been replicated in various different types of outdoor footwear. Also evident from this graph is that while the footwear with the conventional prior art insert warmed at a faster rate than the inventive energy harvesting apparatus, there was a limit to the footwear temperature that could be achieved with the conventional insert (i.e., providing a footwear temperature of about 22° C., and no greater). Inasmuch as the heat generated by the energy harvesting arrangement of the present invention is a function of factors such as the individual's pace, physical design of the apparatus and the chemical properties of the viscous fluid (or strength of the generated eddy current in the resistive heating configuration), the same limitations on maximum achievable temperature do not apply.

Figure 10:
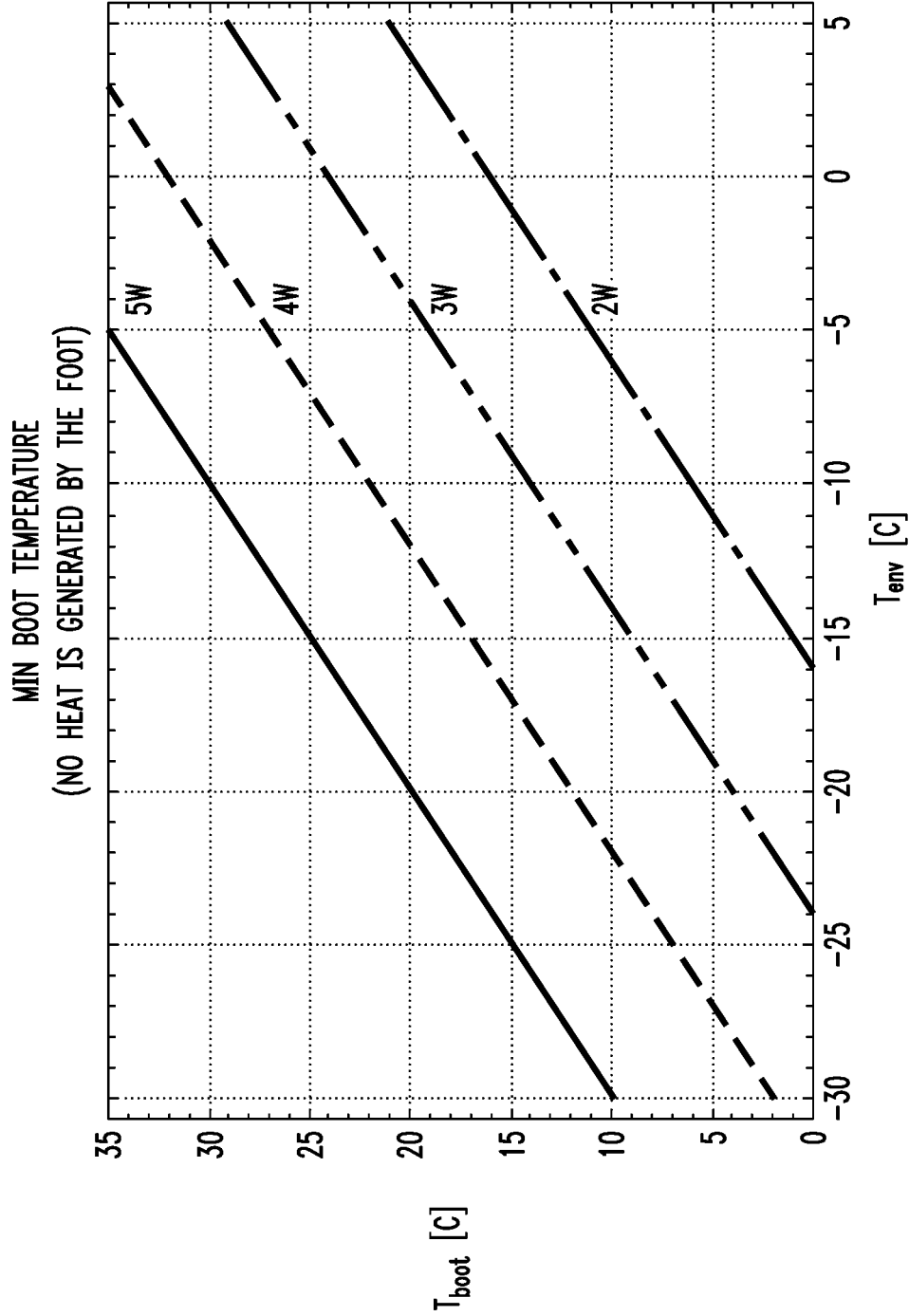
FIG. 10 is a plot of footwear temperature as a function of environmental temperature for various configurations of the inventive apparatus, each configuration associated with a different generated energy level.

FIG. 10 is a plot showing the achievable footwear temperature $T_{boot}$ as a function of the ambient temperature (defined in this plot as the environment temperature $T_{env}$) for several different energy levels, ranging from 2 W to 5 W. Recall that the experimental arrangement used to collect the data of FIG. 7 generated an energy level on the order of 3.3 W. As is clear from the plots of FIG. 8, an arrangement for capturing mechanical energy associated with human locomotion and converting that energy into heat in accordance with the present invention is able to providing heating in footwear at temperatures as low as −15° C. when the user is walking at a pace that creates about 2 W of energy, all the way to a temperature of −30° C. (or lower) when walking at a pace capable of generating about 5 W of energy.

Although only several preferred embodiments of the present invention has been described in detail here, those of ordinary skill in the art should understand that they could make various changes, substitutions and alterations herein without departing from the scope of the invention. In particular, only one exemplary embodiment of the expanding assembly of chain elements is discussed in detail here. However, those of ordinary skill in the art should understand that other embodiments of expanding assemblies of elements based on elastic polymeric materials, mechanical springs, etc. can be advantageously utilized without departing from the scope of the current invention.

What is claimed is:

1. A method of converting mechanical energy into thermal energy for heating footwear, the method including providing an energy harvesting apparatus including a first flexible chamber containing a quantity of liquid, a second flexible chamber containing a quantity of liquid, an energy-generating tube coupled to the first and second flexible chambers wherein the energy-generating tube includes a plurality of segments of conductive material disposed within spaced-apart regions of the tube material along a length thereof such that the liquid flows within the tube between the first and second flexible chambers, and an energy-producing element disposed within the energy-generating tube and comprising an energy-generating chain formed of spaced-apart regions of magnetic material disposed along a flexible string, the energy-generating chain disposed within the energy-generating tube in a manner where the chain slides back and forth within the tube as liquid flows between the first and second flexible chambers, defining multiple areas of overlap between the regions of magnetic material and the segments of conductive material to create eddy currents within the segments of conductive material, the eddy currents generating thermal energy in the form of resistive heat;

applying a mechanical pressure to the first flexible chamber, forcing a portion of the contained liquid into the energy-generating tube, moving the energy-producing element toward the second flexible chamber;

removing the mechanical pressure applied to the first flexible chamber;

applying a mechanical pressure to the second flexible chamber, forcing a portion of the contained liquid into the energy-generating tube, moving the energy-producing element toward the first flexible chamber, and continuing to alternate the application of pressure between the first and second flexible chambers so as to provide movement of the energy-producing element back and forth within the energy-generating tube, converting the applied mechanical pressure into thermal energy.

2. The method as defined in claim 1 wherein human locomotion is used as the source of mechanical energy in the form of applying mechanical pressure in an alternating form to the first and second flexible chambers.

3. The method as defined in claim 1 wherein the first flexible chamber is located in a heel region of a footwear insert and the second flexible chamber is located in a toe region of the footwear insert, with a human locomotion heel strike used to apply mechanical pressure to the first flexible chamber and a human locomotion toe-off used to apply mechanical pressure to the second flexible chamber.

4. The method as defined in claim 1 wherein the energy-producing element of the provided energy harvesting apparatus comprises a viscous liquid of a viscosity sufficient to impart thermal energy to the energy-generating tube as the viscous liquid moves back and forth within the energy-generating tube.

* * * * *